United States Patent
Pedoulias et al.

(10) Patent No.: US 10,420,652 B2
(45) Date of Patent: Sep. 24, 2019

(54) BONE SCAFFOLD IMPROVEMENTS

(71) Applicants: Panagiotis Pedoulias, North Adelaide, South Australia (AU); Matthew James McDonald, North Adelaide, South Australia (AU)

(72) Inventors: Panagiotis Pedoulias, North Adelaide (AU); Matthew James McDonald, North Adelaide (AU); Nathan Christopher Hill, Bedford Park (AU)

(73) Assignees: Dr. Panagiotis Pedoulias (AU); Dr. Matthew McDonald (AU)

( * ) Notice: Subject to any disclaimer, the term of this patent is extended or adjusted under 35 U.S.C. 154(b) by 165 days.

(21) Appl. No.: 15/517,636

(22) PCT Filed: Oct. 9, 2015

(86) PCT No.: PCT/AU2015/000607
§ 371 (c)(1),
(2) Date: Apr. 7, 2017

(87) PCT Pub. No.: WO2016/054682
PCT Pub. Date: Apr. 14, 2016

(65) Prior Publication Data
US 2017/0304073 A1  Oct. 26, 2017

(30) Foreign Application Priority Data
Oct. 9, 2014  (AU) ................. 2014904026

(51) Int. Cl.
| | |
|---|---|
| *A61F 2/44* | (2006.01) |
| *A61B 17/70* | (2006.01) |
| *A61B 17/86* | (2006.01) |
| *A61B 17/16* | (2006.01) |
| *A61F 2/30* | (2006.01) |

(Continued)

(52) U.S. Cl.
CPC ........ *A61F 2/4455* (2013.01); *A61B 17/1635* (2013.01); *A61B 17/68* (2013.01);
(Continued)

(58) Field of Classification Search
CPC .. A61F 2/44; A61F 2/4455; A61F 2/30; A61F 2/30771; A61F 2/30734;
(Continued)

(56) References Cited

U.S. PATENT DOCUMENTS

| | | |
|---|---|---|
| 5,439,684 A | 8/1995 | Prewett et al. |
| 6,706,067 B2 | 3/2004 | Shimp et al. |

(Continued)

FOREIGN PATENT DOCUMENTS

| | | |
|---|---|---|
| EP | 0424159 A2 | 4/1991 |
| WO | WO 98/38918 | 9/1998 |

(Continued)

OTHER PUBLICATIONS

International Search Report and Written Opinion prepared by the Australian Patent Office dated Dec. 10, 2015, for International Application No. PCT/AU2015/000607.
(Continued)

*Primary Examiner* — Christopher J Beccia
(74) *Attorney, Agent, or Firm* — Sheridan Ross P.C.

(57) ABSTRACT

Bone graft scaffold arrangements are described that can be used in minimally invasive posterolateral spinal fusion. The bone graft scaffold apparatus comprise a housing which comprises a cavity for receiving bone growth promoting materials and a plurality of apertures. In use these allow bone and blood vessels to grow through the plurality of apertures to form the bone bridge between vertebrae. Further the bone graft scaffold apparatus comprise at least one opening in the housing for receiving a shaft of an orthopaedic device, such as rod linking pedicle screws, or the shaft of a pedicle screw, or another suitable shaft in another surgical procedure. The apparatus can be attached to struc-
(Continued)

tural components such as rods and screws and used to form a continuous scaffold between vertebras to assist in forming a bone bridge.

23 Claims, 10 Drawing Sheets

(51) Int. Cl.
  A61B 17/68 (2006.01)
  A61B 17/84 (2006.01)
  A61B 17/00 (2006.01)
  A61F 2/28 (2006.01)
(52) U.S. Cl.
  CPC ...... *A61B 17/7002* (2013.01); *A61B 17/7032* (2013.01); *A61B 17/7035* (2013.01); *A61B 17/7098* (2013.01); *A61B 17/842* (2013.01); *A61B 17/8695* (2013.01); *A61F 2/30734* (2013.01); *A61F 2/30771* (2013.01); *A61B 2017/00915* (2013.01); *A61F 2002/2835* (2013.01); *A61F 2002/3068* (2013.01); *A61F 2002/3093* (2013.01); *A61F 2002/30224* (2013.01); *A61F 2002/30227* (2013.01); *A61F 2002/30233* (2013.01); *A61F 2002/30622* (2013.01); *A61F 2002/30787* (2013.01)
(58) Field of Classification Search
  CPC .......................... A61B 17/70; A61B 17/7032; A61B 17/7035; A61B 17/86; A61B 17/8695; A61B 17/7002
  See application file for complete search history.

(56) References Cited

U.S. PATENT DOCUMENTS

| | | | |
|---|---|---|---|
| 6,863,694 | B1 | 3/2005 | Boyce et al. |
| 7,344,564 | B2 * | 3/2008 | Sweeney ................. A61F 2/446 623/17.11 |
| 7,404,818 | B2 | 7/2008 | Miller et al. |
| 7,662,185 | B2 | 2/2010 | Alfaro et al. |
| 8,449,545 | B2 | 5/2013 | Sidebotham et al. |
| 2003/0023308 | A1 | 1/2003 | Leroux et al. |
| 2005/0112397 | A1 | 5/2005 | Rolfe et al. |
| 2005/0244239 | A1 | 11/2005 | Shimp |
| 2005/0273166 | A1 | 12/2005 | Sweeney |
| 2006/0111724 | A1 | 5/2006 | Yueng Wai Ping |
| 2010/0222750 | A1 | 9/2010 | Cheng |
| 2011/0004251 | A1 | 1/2011 | Sweeney et al. |
| 2011/0087296 | A1 | 4/2011 | Reiley et al. |
| 2012/0316649 | A1 | 12/2012 | Johnsoton et al. |
| 2013/0274890 | A1 | 10/2013 | McKay |
| 2013/0297027 | A1 * | 11/2013 | Cowan ................. A61F 2/4455 623/17.14 |
| 2014/0257408 | A1 | 9/2014 | Trieu et al. |
| 2014/0277569 | A1 | 9/2014 | Lange |

FOREIGN PATENT DOCUMENTS

| | | |
|---|---|---|
| WO | WO 2000/025706 A1 | 5/2000 |
| WO | WO 2012/109620 A2 | 8/2012 |

OTHER PUBLICATIONS

Delloye et al: "Bone Allografts. What They Can Offer and What They Cannot." The Journal of Bone & Joint Surgery (Br); vol. 89-B, No. 5, May 2007, pp. 574-580.
Webpage: "Viper 2 MIS Spine System_DePuy Synthes Companies" (from www.depuysynthes.com/hcp/spine/products/qs/VIPER-2-MIS-Spine-System). Downloaded Mar. 31, 2017.
Webpage: Zimmer Spine _ PathFinder® NXT Minimally Invasive Pedicle Screw System for Spinal Surgery (from www.zimmer.com.au/medical-professionals/products/spine/pathfinder-minimally-invasive-pedicle-screw.html ). Downloaded Mar. 31, 2017.
Medtronic CD Horizon Longitude Multi-Level Percutaneous Fixation System; 2008.

* cited by examiner

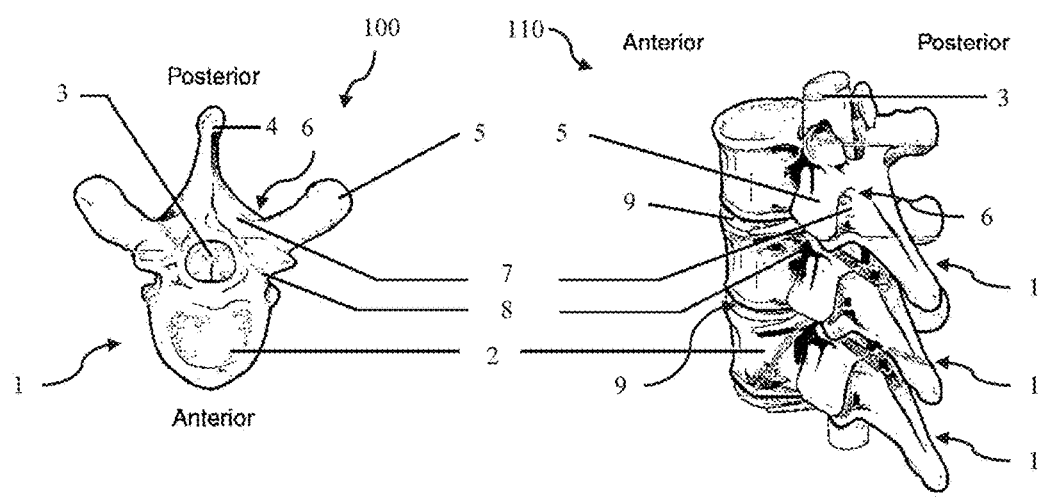
Figure 1A
Figure 1B
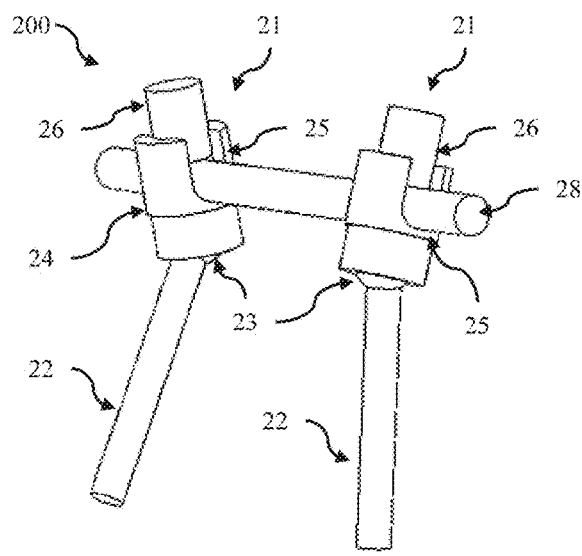
Figure 2A

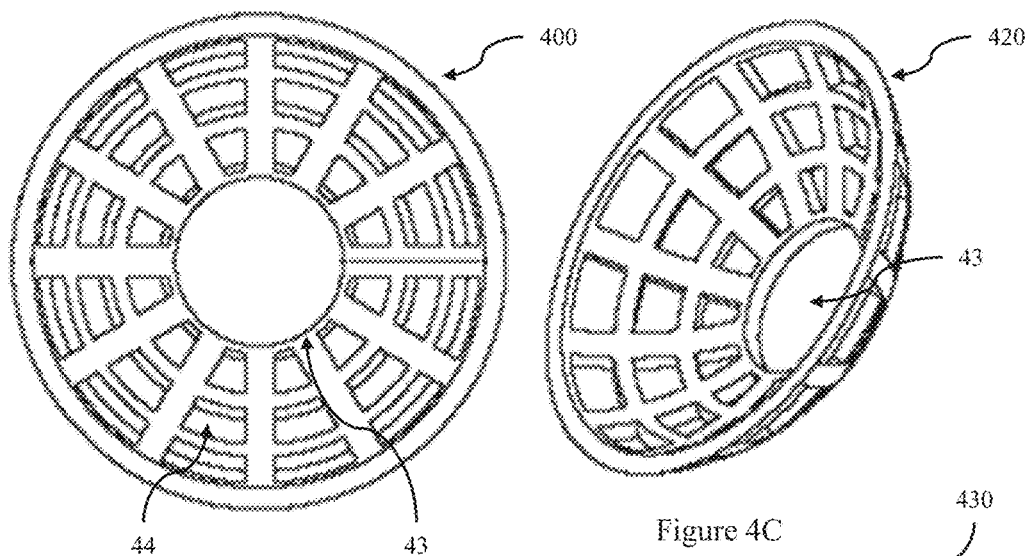
Figure 4A
Figure 4C
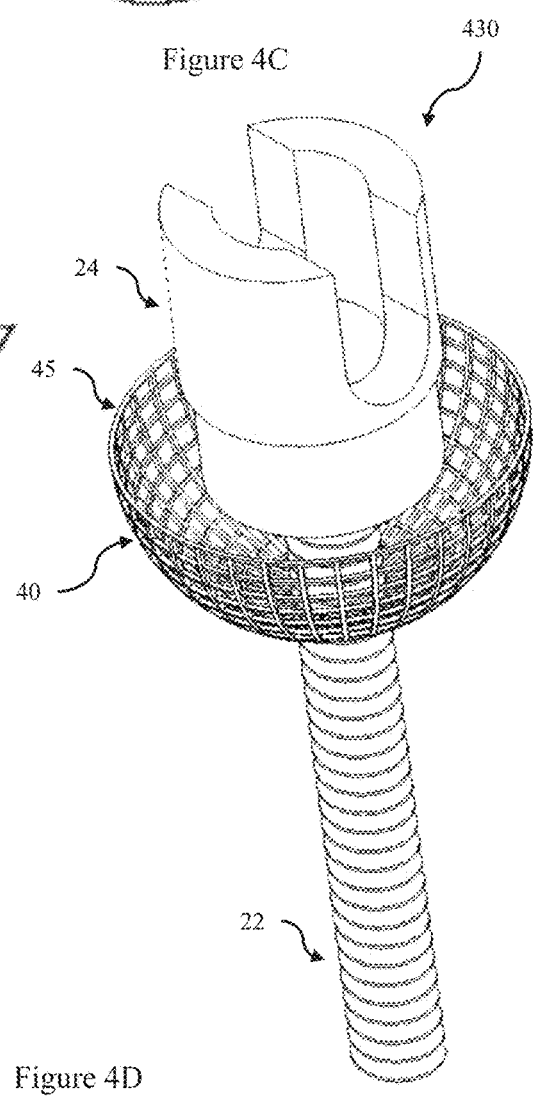
Figure 4B
Figure 4D

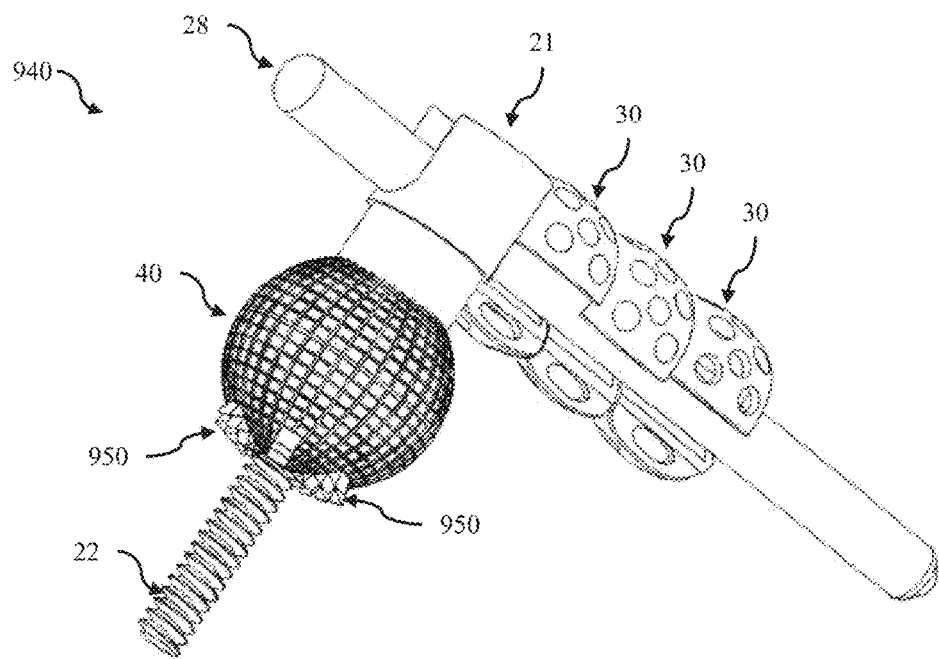
Figure 9E
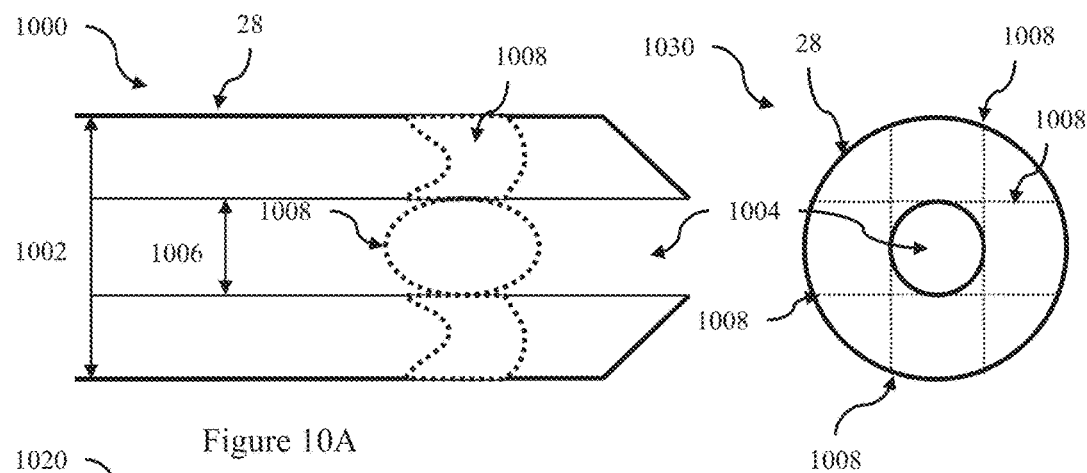
Figure 10A
Figure 10B
Figure 10C

BONE SCAFFOLD IMPROVEMENTS

CROSS-REFERENCE TO RELATED APPLICATIONS

This application is a national stage application under 35 U.S.C. 371 and claims the benefit of PCT Application No. PCT/AU2015/000607 having an international filing date of 9 Oct. 2015, which designated the United States, which PCT application claimed the benefit of Australian Provisional Patent Application No. AU2014904026 titled "Bone Scaffold Improvements" and filed on 9 Oct. 2014, the disclosure of each of which are incorporated herein by reference.

TECHNICAL FIELD

The present disclosure relates to orthopaedic devices. In a particular form the present disclosure relates to orthopaedic devices for minimally invasive posterolateral spinal fusion procedures.

BACKGROUND

Spinal fusion surgical procedures involve rigidly fixing two or more vertebrae together in order to alleviate back pain or correct spinal malalignments or degenerative conditions. FIG. 1A shows a top or superior view 10 of a vertebra 1 comprising a body 2, the spinal cord 3, spinous process 4, transverse process 5 and vertebral arch 6 comprising lamina 7 and pedicle 8. FIG. 1B further shows a left posterolateral view 11 of articulated vertebrae 1 each separated by intervertebral disc 9. Spinal fusion surgery normally involves insertion of a rigid orthopaedic structural implant, which may also be referred to as an orthopaedic device or support, and laying bone graft material around the implants in order to promote subsequent growth of a rigid bone graft (or bridge) to permanently fix the two or more vertebrae together. The rigid structural implants may be left in place, or be removed at a later date once the rigid bone graft has grown.

There are two main types of spinal fusion surgery which differ in the location/position of the structural implants and location of bone graft material. In an interbody spine fusion the bone graft is placed in between the vertebral bodies where the intervertebral disc 9 usually lies. The intervertebral disc 9 has to be partially cut away or completely removed and endplates cleaned prior to placement of a structural support and the graft material. This will allow the fusion to occur from one vertebral body to the other through their endplates (ie from one body 2 to the next body 2). In a posterolateral fusion, the bone graft links the transverse process 6 of one vertebra to the transverse process of the next vertebra. The most common fixation technique employed is pedicle screw fixation. In this procedure the surgeon makes an incision in the midline of the back and the back muscles surrounding the spine are then retracted to the side to expose the posterolateral area and to create a bed for the bone graft. Traditionally the area between the adjacent transverse processes has been an ideal place to achieve bony union between vertebra. Screws are placed within the pedicles of adjacent vertebral segments and are then connected with a metal rod (typically titanium, or a titanium alloy). This is performed on one side of the spine or both sides of the spine (ie bilaterally) and may span two or more vertebra. For example a one level bilateral fusion would use four screws and two rods to fuse two vertebrae and a two level bilateral fusion would use six screws and two rods to fuses three vertebrae. FIG. 2A is a perspective view of an illustrative example of a one level pedicle screw and rod arrangement 20. In this example each pedicle screw 21 comprises a threaded shaft 22 attached to a crown 24, and a lock screw 26. The shaft 22 and crown 24 are provided as a single component (ie parts may be manufactured individually and then assembled into a single component part) in which the crown comprises a cavity and an aperture in its base through which shaft 22 passes. The upper end of the shaft 22 ends in a ball 23 with a diameter larger than the aperture to retain and link the shaft 22 to the crown 24. This allows relative movement of the shaft with respect to the crown. The crown further comprises a U shaped saddle 25 to receive a rod 28 which is used to link adjacent pedicle screws (and thus vertebra). The depth of the saddle cut-out rod 23 is such that the rod 28 is located above the ball 23. A locking screw 26 is inserted into the top of the crown to lock the rod in place. This arrangement can be installed in parts (eg shaft 22 and crown 24 component, then rod 28, and then locking screw 26), and allows flexible installation as each pedicle screw 21 can be orientated at a different angle to the other pedicle screws 21. Other variants of pedicle screw systems may use variants (for example the shaft and crown may be manufactured as a single part with the shaft in a fixed orientation with respect to the crown. Bone graft promoting materials, either taken from the patient, a cadaver or synthetically generated (or some combination of the three sources) is laid out on the exposed posterolateral area and around the rods and screws, and the muscles are laid back down over the graft and the incision closed. The bone graft promoting materials include bone fragments, tissue or similar material, and or a solution containing bone morphogenic protein (BMP) or materials soaked or infused with BMP. FIG. 2B is a top view of an open surgery two level fusion 210 illustrating the laying of bone graft material 15 around the rods 28. In some cases a laminectomy may also be performed in which a portion of the lamina is removed to expose the nerves and spinal cord 3. Over the next few months, the bone graft material 15 and adjacent transverse processes 5 and vertebral bodies 2 will gradually fuse into a single rigid bone structure.

The treatment of spinal conditions with Minimally Invasive Surgery (MIS) has, or is rapidly becoming, the preferred method due to the reduced risk of complications and reduced recovery time. Some studies of MIS Spine surgery have reported benefits including reduced blood loss, less infection, less post-operative pain and reduced hospital stays, benefits which also enable complex surgery to be performed on older and sicker patients.

However up until recently posterolateral fusion has only been possible through open surgery where trauma may occur to tissue surrounding the vertebrae. In a MIS posterolateral fusion, case stab incisions are made only above the screw incision points, and the linking rod is pushed through the tissue between the incision points. That is, tissue surrounding the rod and between the two pedicle screws is not exposed, and thus bone graft promoting material cannot be delivered along the path along which the bone growth is desired. Thus in prior attempts at MIS posterolateral fusion procedures generally no attempt is made for bony fusion. This may lead to instrumentation failure and pseudoarthrosis, and removal of instrumentation. There is thus a need to develop devices to enable MIS for posterolateral fusion, or to at least provide surgeons with a useful alternative to current surgical methods for posterolateral fusion.

SUMMARY

According to a first aspect, there is provided a bone graft scaffold apparatus comprising:
   a housing comprising:
      a cavity for receiving bone growth promoting materials; and
      a plurality of apertures, which in use allow bone growth promoting material to move out into the surrounding tissue through the plurality of apertures and/or to allow bone to grow through the plurality of apertures; and
   at least one opening in the housing for receiving a shaft of an orthopaedic device.

In one form, the housing is a clip configured to clip onto a shaft of an orthopaedic device.

In one form, the housing is a C shaped clip structure comprising a first side wall, an opposing second side wall, and an outer wall spanning the first side wall and opposing second side wall, and wherein the at least one opening extends inward from the outer wall to receive the shaft such that in use the received shaft extends through the first side wall and the opposing second side wall.

In one form, the bone graft scaffold apparatus further comprises an attachment projection from a first side wall, and a corresponding receiving structure on the second side wall, such that in use, the attachment projection from a first bone graft scaffold apparatus engages with the receiving structure in a second adjacent bone graft scaffold apparatus to secure and align the first and second bone graft scaffold apparatus.

In one form, the attachment projection comprises a shelf and a flange, and the receiving structure comprises a slot for receiving the flange.

In one form, the housing is a washer comprising a central aperture configured to receive a shaft of a pedicle screw and at least one upturned portion extending away from the central aperture to define the cavity.

In one form, the housing is a conical washer having a rotationally symmetric upwardly curved profile.

In one form, the bone graft scaffold apparatus further comprises a cap.

In one form, the bone graft scaffold apparatus further comprises a plurality of cutting projections projecting from the base upturned portion adjacent the shaft.

In one form, the housing is manufactured from a porous or absorbent material such that prior to use the bone graft scaffold is soaked in a bone growth promoting agent to absorb the bone growth promoting agent so that in use the bone growth promoting reagent will leach out of the housing.

In one form, the housing is a mesh and the plurality of apertures are interstitial spaces in the mesh.

In one form, the shaft supports the housing.

In one form, the bone graft scaffold apparatus is coated with a bone growth promoting agent.

In one form, the bone graft scaffold apparatus is constructed from a biocompatible radio translucent polymer.

According to a second aspect, there is provided an orthopaedic device comprising:
   at least one rod;
   at least two pedicle screws;
   a plurality of bone graft scaffold apparatus according to the first aspect.

According to a third aspect, there is provided a method for performing surgery comprising:
   filling one or more bone graft scaffold apparatus according to the first aspect with bone growth promoting materials;
   inserting a first pedicle screw into a pedicle of a first vertebra;
   inserting a second pedicle screw into a pedicle of a second vertebra;
   inserting a rod between the first pedicle screw and the second pedicle screw; and
   attaching the one or more graft scaffold apparatus to the rod, the first or the second pedicle screw.

According to a fourth aspect, there is provided a decorticator apparatus comprising:
   a substantially circular hollow body having a central axis and tapering at a distal end;
   a plurality of directional blade projections located at about the periphery at the distal end, wherein each blade projection comprises a cup ending in a cutting edge such that rotation about the central axis in a first direction directs the cutting edge into surrounding tissue to cut the surrounding tissue, and rotation about the central axis in an opposite direction directs the cup into the surrounding tissue;

In one form, in profile, each cup extends over an arc of greater than 90°.

In one form, a tip of the substantially circular hollow body comprises a central aperture and each directional blade projection comprises an aperture extending into a collection cavity in the substantially circular hollow body, and so that in use at least a portion of the material cut from surround tissue is collected within the collection cavity.

In one form, a proximal end of the substantially circular hollow body comprises a thread to allow attachment to a dilator tube.

BRIEF DESCRIPTION OF DRAWINGS

Embodiments of the present disclosure will be discussed with reference to the accompanying drawings wherein:

FIG. 1A shows a top view of a vertebra;

FIG. 1B shows a left posterolateral view of articulated vertebrae;

FIG. 2A is a perspective view of a one level pedicle screw and rod arrangement;

FIG. 4A is a top view of a of a bone graft scaffold apparatus according to an embodiment;

FIG. 4B is a side view of the bone graft scaffold apparatus of FIG. 4A;

FIG. 4C is an isometric view of the bone graft scaffold apparatus of FIG. 4A;

FIG. 4D is an isometric view of the bone graft scaffold apparatus of FIG. 4A fitted to a pedicle screw according to an embodiment;

FIG. 9E is a perspective view of a pedicle screw arrangement fitted with the ellipsoid cage embodiment of a bone graft scaffold apparatus of FIGS. 9C and 9D and clip embodiments of a bone graft scaffold apparatus fitted to the rod according to an embodiment;

FIG. 10A is a side profile view of an end of a hollow rod according to an embodiment;

FIG. 10B is an end view the hollow rod shown in FIG. 10A; and

FIG. 10C is a three-quarter section view of an end of a hollow rod showing a spout hole arrangement for bone graft material dispersion according to an embodiment.

In the following description, like reference characters designate like or corresponding parts throughout the figures.

DESCRIPTION OF EMBODIMENTS

A major challenge for MIS posterolateral spinal fusion is delivering bone graft material adjacent to the rod and pedicle screws where there is limited access and the area is surrounded by muscle and connective tissue. Various embodiments of bone graft scaffold arrangements will now be described that can be used in MIS posterolateral spinal fusion, along with other orthopaedic surgical procedures including open posterolateral spinal fusion and interbody spinal fusion, or to assist in delivering bone graft material along a desired path or specific region. Embodiments of the bone graft scaffold apparatus comprise a housing which comprises a cavity for receiving bone growth promoting materials and a plurality of apertures. In use these allow bone growth material to move out into the surrounding tissue (eg by leaking or leaching out, or via mechanical or compressive forces forcing material out of the cavity) and/or bone (and blood vessels) to grow through the plurality of apertures, to promote formation of the bone bridge between vertebrae. Further the bone graft scaffold apparatus comprise at least one opening in the housing for receiving a shaft of an orthopaedic device, such as rod linking pedicle screws, or the shaft of a pedicle screw, or another suitable shaft in another surgical procedure. Additionally embodiments of decorticator apparatus are described which can be used to prepare the site and/or collect bone fragments and tissue which may be placed in the bone graft scaffold apparatus to promote growth of the bony bridge.

Figure 2B:
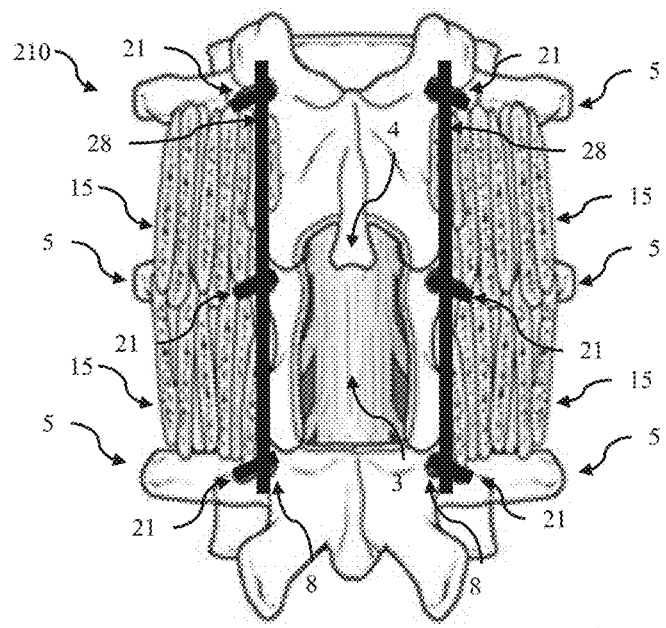
FIG. 2B is a top view of an open surgery two level fusion illustrating the laying of bone graft material around the rods.
Figure 3:
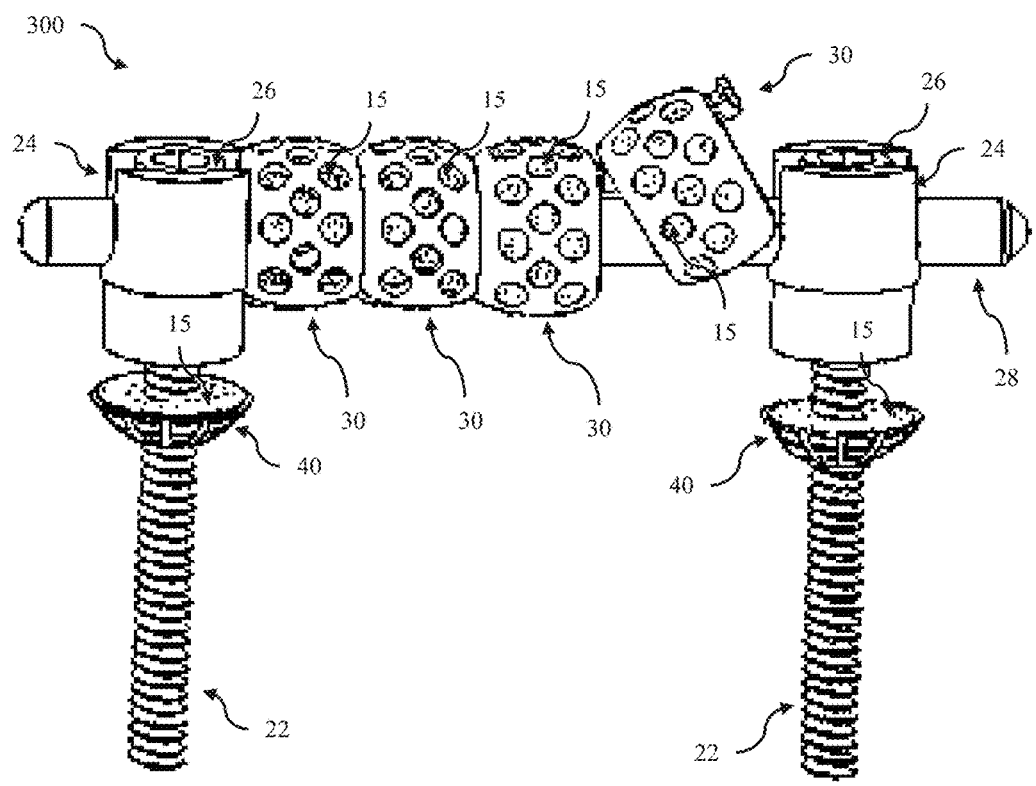
FIG. 3 is a perspective view of a bone graft scaffold apparatus attached to a pedicle screw arrangement according to an embodiment.

FIG. 3 is a perspective view 300 illustrating a conical washer 40 and clip 30 embodiments of bone graft scaffold apparatus attached to the pedicle screw arrangement shown in FIG. 2A. However as will be apparent the bone graft scaffold apparatus may be used with other pedicle screw arrangements such as pedicle screws comprised of a shaft and crown. The conical washer embodiment 40 is further illustrated in FIGS. 4A to 4D and may be fitted around the shaft 22 of pedicle screws 21. The clip embodiment 30 is further illustrated in FIGS. 5A to 5E and may be fitted to an in situ rod 28, or in an open procedure it could be fitted to the rod prior to insertion. Bone graft promoting materials 15 are inserted into cavities in bone graft scaffold apparatus and each provide a scaffold structure or template for growth as well as a means of introducing bone graft material along the rods and around the pedicle screws. Whilst each can be used independently of each other, using both the clips and washers provides a continuous scaffold between vertebras to assist in forming a bone bridge along a desired path. Additionally bone graft material can be injected or inserted around the head of the pedicle screw to further assist in forming the bone bridge. Additionally, the scaffold apparatus may be coated with bone growth promoting materials, be surface treated for example by creating pores or surface texture to promote bone growth, or the scaffold apparatus may be constructed of a material that will absorb and subsequently leak or leach out bone growth promoting materials.

In one embodiment the bone graft scaffold apparatus is a washer like arrangement 40 comprising a central aperture 43 configured to receive a shaft of a pedicle screw 22 and at least one upturned portion extending away from the central aperture to define the cavity. FIG. 4A is a top view 400 of a of a bone graft scaffold apparatus according to an embodiment in which the housing is a conical washer having a rotationally symmetric upwardly curved profile. FIG. 4B shows a side view 410, FIG. 4C is an isometric view 420, and an isometric view of the bone graft scaffold apparatus fitted to a pedicle screw 430 according to an embodiment. In this embodiment the upturned portion of the washer comprises a plurality of radial spokes 41 and concentric ribs 42 defining a plurality of apertures 44 between the spokes 41 and ribs 42. The interior of the washer defines the cavity in which bone graft promoting materials may be placed. As illustrated in FIG. 4D this delivers and contains bone graft promoting material close to the pedicle screw insertion point such that the top or upper edge of the upturned portion is proximal to or may even extend above the base of the crown 24.

In one embodiment the diameter is 13.3 mm and the inner diameter (central aperture 43) is 4.5 mm, and the depth (height) is 3.7 mm. The spokes and ribs may have thicknesses of 0.8 mm. However these dimensions are illustrative only and other dimensions may be used.

Usage is as follows. The shaft 22 of the pedicle screw 23 is inserted through the central aperture 43 of the washer 40, and bone graft material is loaded into the cavity in the washer 40. The shaft 22 (and connected crown 24) and washer 40 are then inserted through the key hole incision to the pedicle and the screw is drilled into the pedicle of the vertebra. During drilling the washer is sandwiched between the pedicle and the crown of the pedicle screw, which may force some of the bone graft material to either be extruded out of apertures 44, or over the top edge 45, thus assisting in forming a continuous bridge of bone graft promoting materials.

Figures 5A, 5B, 5C, 5D, 5E:
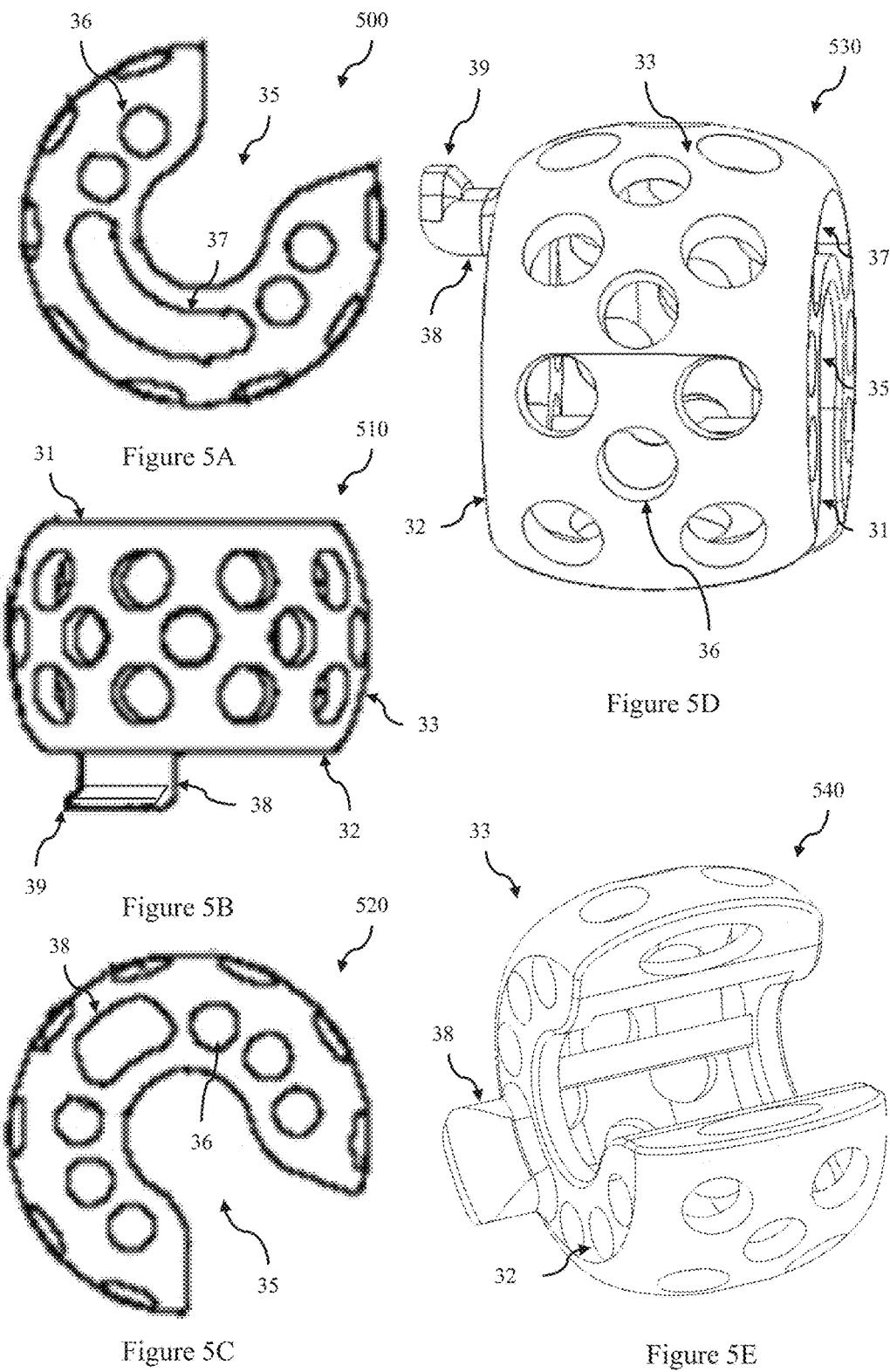
FIG. 5A is a first side view of a bone graft scaffold apparatus according to an embodiment.
FIG. 5B is an top perspective view of the bone graft scaffold apparatus of FIG. 5A.
FIG. 5C is a second side view of the bone graft scaffold apparatus of FIG. 5A.
FIG. 5D is an end perspective view of the bone graft scaffold apparatus of FIG. 5A.
FIG. 5E is a bottom perspective view of the bone graft scaffold apparatus of FIG. 5A.

In another embodiment the housing of the bone graft scaffold apparatus is a clip 30 configured to clip onto a shaft (or clasp the shaft) of an orthopaedic device such as a rod 28 or screw shaft 2. FIG. 5A is a first side view 500 of a clip embodiment 30 of a bone graft scaffold apparatus for attachment to a rod 28. FIG. 5B is an top perspective view 510, FIG. 5C is a second side view 520, FIG. 5D is an end perspective view 530 and FIG. 5E is a bottom perspective view 540 of the bone graft scaffold apparatus of FIG. 5A. In this embodiment, the housing is a C shaped clip structure comprising a first side wall 31, an opposing second side wall 32, and an outer wall 33 spanning the first side wall 31 and opposing second side wall 32. An opening 35 extends inward from the outer wall 33 to receive the shaft of the rod 28 such that in use the received shaft extends through the first side wall 31 and the opposing second side wall 32. The inner wall or surface 34 is largely open, and in this embodiment comprises a plurality of ribs or members extending between the first and second side walls to allow bone graft material in the cavity in the housing to contact the rod 28. The radius of the inner wall or surface is selected to approximately match the intended rod diameter, and may be equal or slightly smaller or larger to control the amount of spring or gripping force applied by the clip to the rod and thus to control the ease with which an attached clip may be rotated around the rod, or moved along the rod. The clips may be designed to clip onto standard or common diameter rods such as those in the range 4 mm to 7 mm (eg 4 mm, 4.5 mm, 5 mm, 5.5 mm, 6 mm, 6.5 mm, 7 mm), or the clip may be designed to clip onto a custom size, including those smaller than 4 mm or larger than 7 mm (eg 8 mm, 9 mm, 10 mm, 15 mm etc) The outer wall 33 and side walls 31, 32 each contain a plurality of apertures to allow bone grown material to leak or extrude out (eg on insertion on the rod) and allow growth through the clip (which acts as a scaffold).

In this embodiment the clip 30 further comprises an attachment projection 38 from the first side wall 31, and a corresponding receiving structure 37, on the second side wall 32. In use, the attachment projection from a first clip engages with the receiving structure in a second clip. This secures the two clips together and also aligns the two clips. In this embodiment the attachment projection 38 comprises a shelf and a flange, and the receiving structure comprises a slot 37 for receiving the flange 39. The shelf and flange act as a lever clip.

In one embodiment the clip is designed to clip onto a 5.5 mm diameter rod, and the clip has a width of 10 mm, the arc of the outer surface spans 280° and the radius is 7.75 mm (ie diameter of 15.5 mm, and the radius to the inner surface is 2.75 mm (ie diameter 5.5 mm). The arc of the attachment projection spans 32° and the arc of the slot 37 spans 97°. The apertures are 2 mm in diameter. However these dimensions are illustrative only and other dimensions may be used.

Figure 6A:
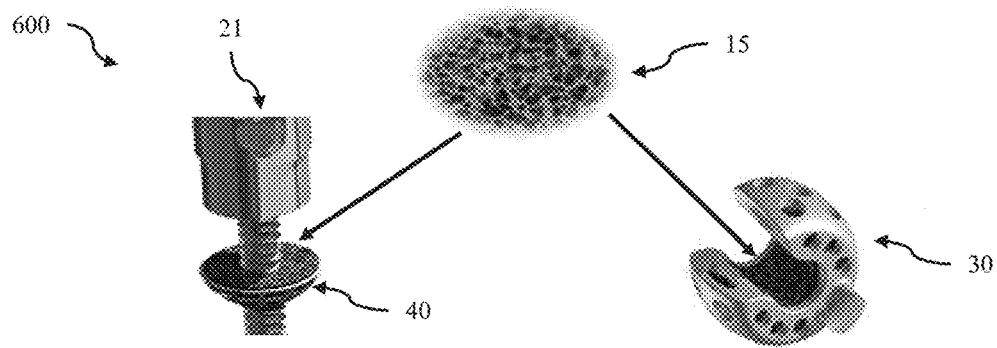
FIG. 6A is a perspective view illustrating insertion of bone growth promoting material into a washer embodiment of the bone graft scaffold apparatus and a clip embodiment of the bone graft scaffold apparatus.
Figure 6B:
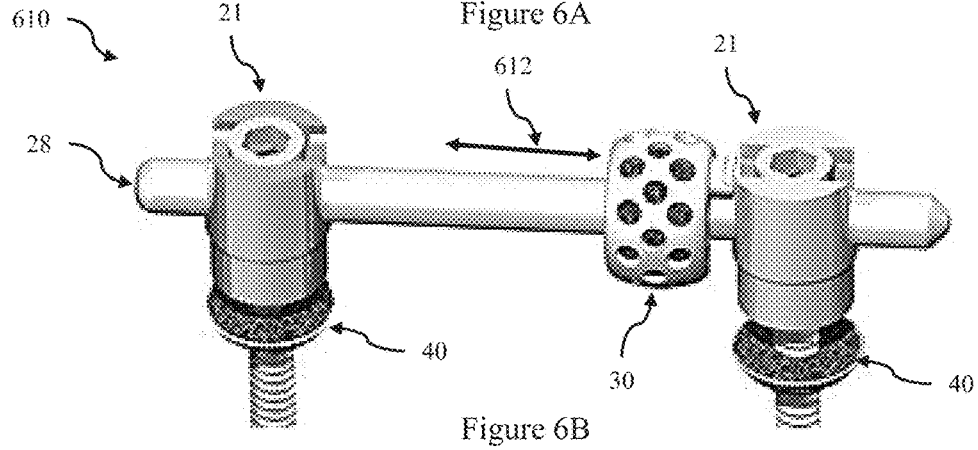
FIG. 6B is a perspective view illustrating placement of a first clip embodiment of the bone graft scaffold apparatus filled with bone growth promoting material to a rod of a pedicle screw arrangement according to an embodiment.

FIGS. 6A to 6D further illustrate use of the washer 40 and clip 30 embodiments in a pedicle screw arrangement. For the purposes of clarity the vertebrae and surrounding tissues have been omitted. FIG. 6A is a perspective view 600 illustrating insertion of bone growth promoting material 15 into a washer embodiment 40 of the bone graft scaffold apparatus and a clip embodiment 30 of the bone graft scaffold apparatus. FIG. 6B is a perspective view 610 illustrating placement of a first clip 30 filled with bone growth promoting material 15 onto rod 28. The filled clip is inserted through the key-hole incision, and clipped onto the in situ rod (via opening 35 which receives the shaft of the rod 28). It can then be pushed along the rod through the region between key-hole incisions which would otherwise be inaccessible as shown by arrows 612. The inner diameter and shape of the clip can be designed to fit predetermined rod sizes including 4.5 mm, 5 mm, 5.5 mm, 6 mm, 6.5 mm, and 7 mm diameter rods, although it is to be understood that rods outside of this range, including custom sized rods may also be used.

Figure 6C:
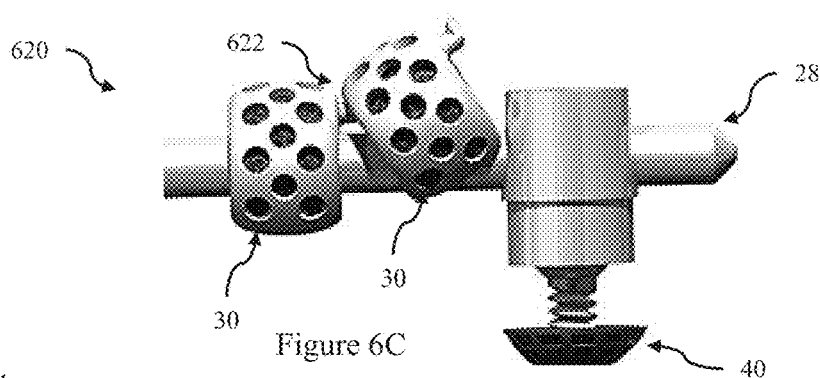
FIG. 6C is a perspective view illustrating attachment of a second clip embodiment of the bone graft scaffold apparatus to the rod and the first clip illustrated in FIG. 6B.
Figure 6D:
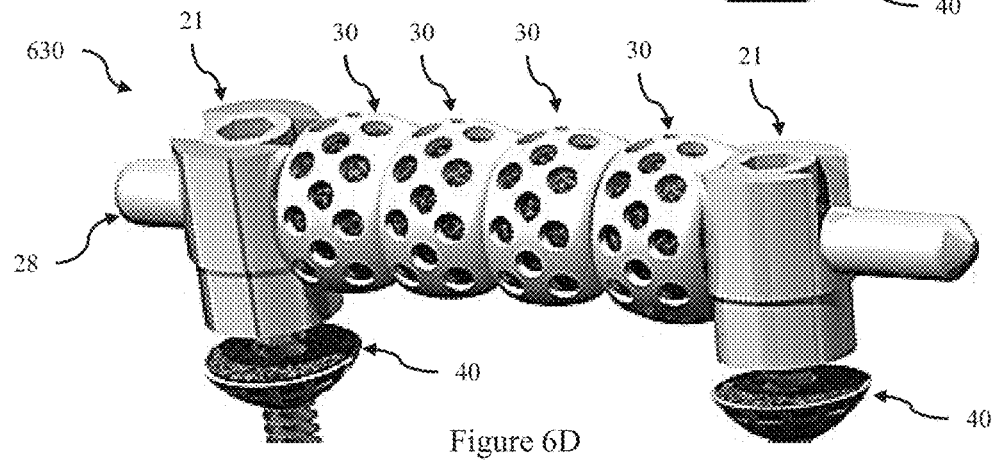
FIG. 6D is a perspective view illustrating four clip embodiments of the bone graft scaffold apparatus attached to the to the rod in FIG. 6B.

FIG. 6C is a perspective view illustrating attachment of a second clip embodiment of the bone graft scaffold apparatus to the rod and the first clip illustrated in FIG. 6B. In this case as the clip is clipped onto the rod, the flange 39 is inserted into and levered into (and received by) the slot 37. This draws the two clips together and ensures they have the same alignment. The clips can then be pushed along the rod, and additional clips added. FIG. 6D is a perspective view 630 illustrating four clips attached to the rod (and each other) to form a continuous bridge or scaffold between pedicle screws. Once fitted the clips can be rotated, for example to expose the opening 35 and allow access to the rod (that is attachment projections 38 are proximal to the vertebra). This may facilitate later removal of the rod if required. The clips are similar in size to other components and thus can be delivered using existing delivery devices, or using modified delivery devices which can grip the clips and push them onto the rods.

A further step in posterolateral spinal fusion grafting involves preparation of the bone for grafting. This involves decortification of the medial portion of the transverse process and facet joint. In the case MIS, this requires decortification to be performed through the key-hole incision. To further assist, a reamer like decorticator apparatus 50 was also developed. Unlike reamers used in other orthopaedic surgeries such as hip implants the reamer 50 comprises directional blades which are designed to only abrade the bone surface and is not intended to create a large cavity in bone. Further the directionality of the blades allows the surgeon to control when cutting is performed in order to minimise any damage to surrounding tissue whilst delivering the decorticator to the target decortication site.

Figures 7A, 7B:
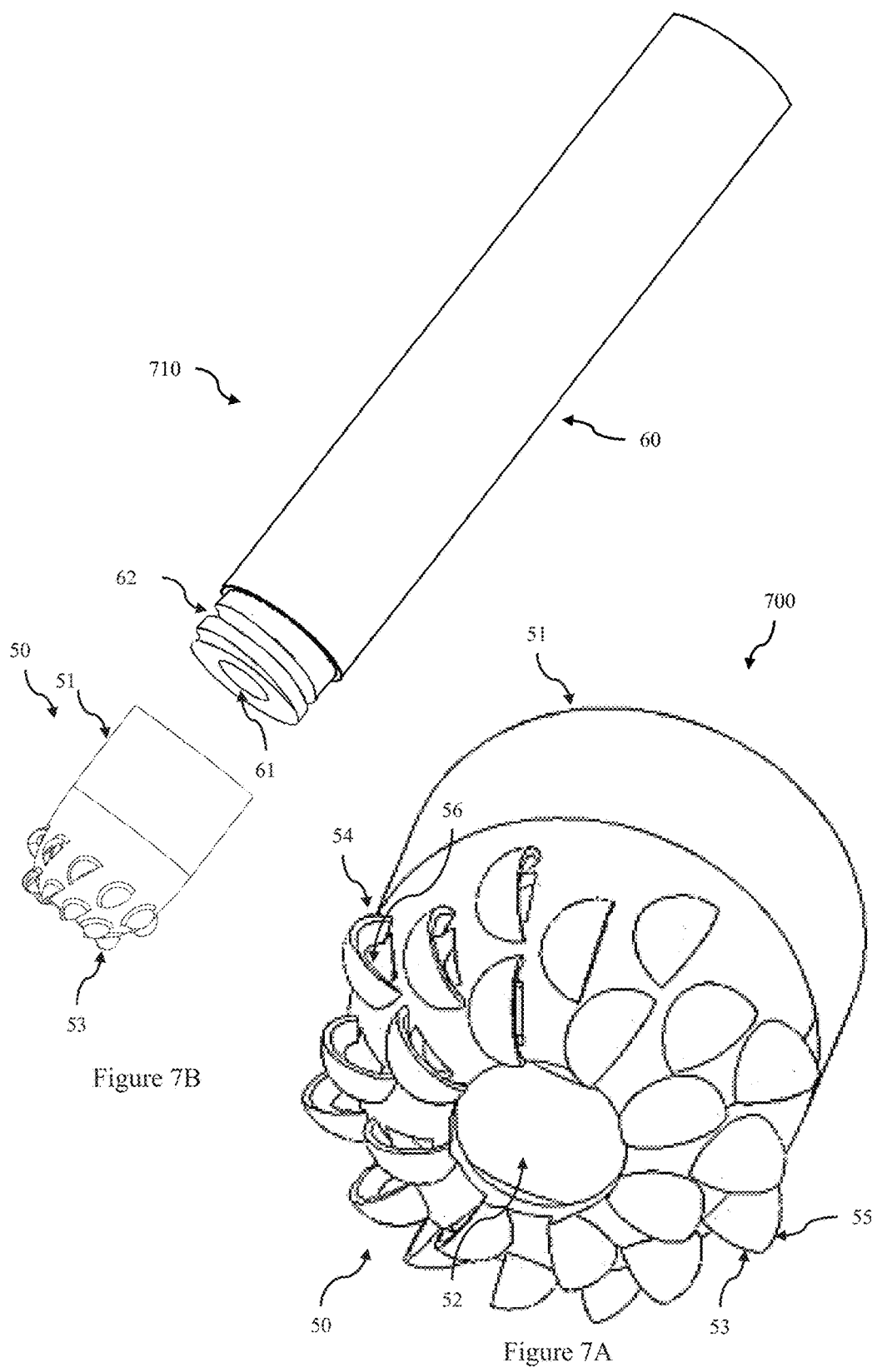
FIG. 7A is an isometric end view of a decorticator apparatus according to an embodiment.
FIG. 7B is an isometric view of the decorticator apparatus of FIG. 7A and a shaft according to an embodiment.
Figures 7C, 7D:
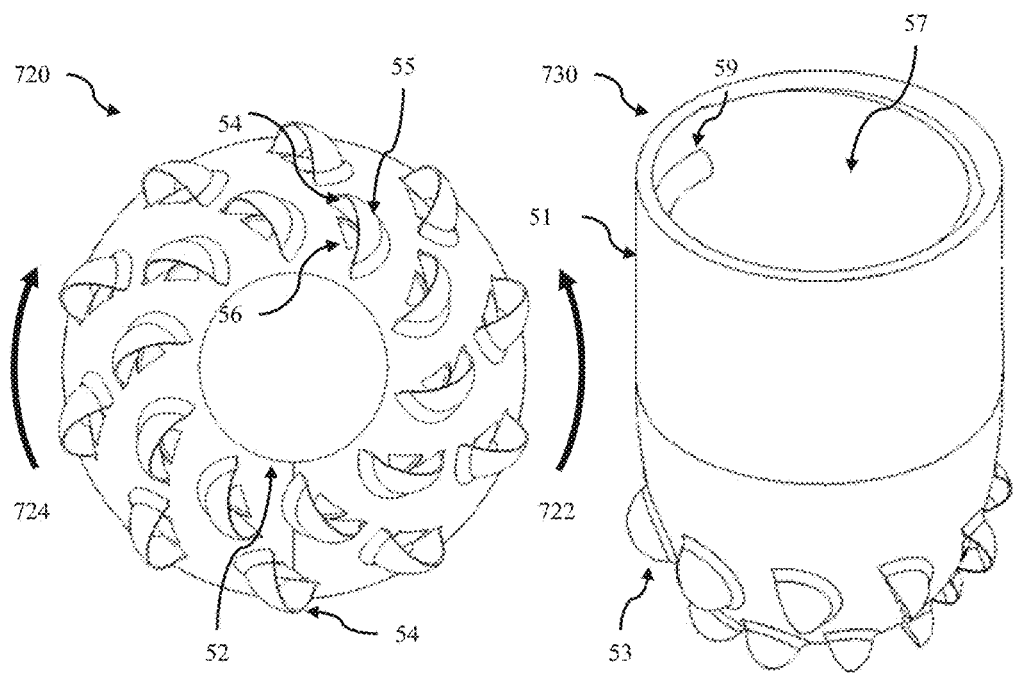
FIG. 7C is an end view of the decorticator apparatus of FIG. 7A.
FIG. 7D is an side isometric view of the decorticator apparatus of FIG. 7A.
Figures 7E, 7F:
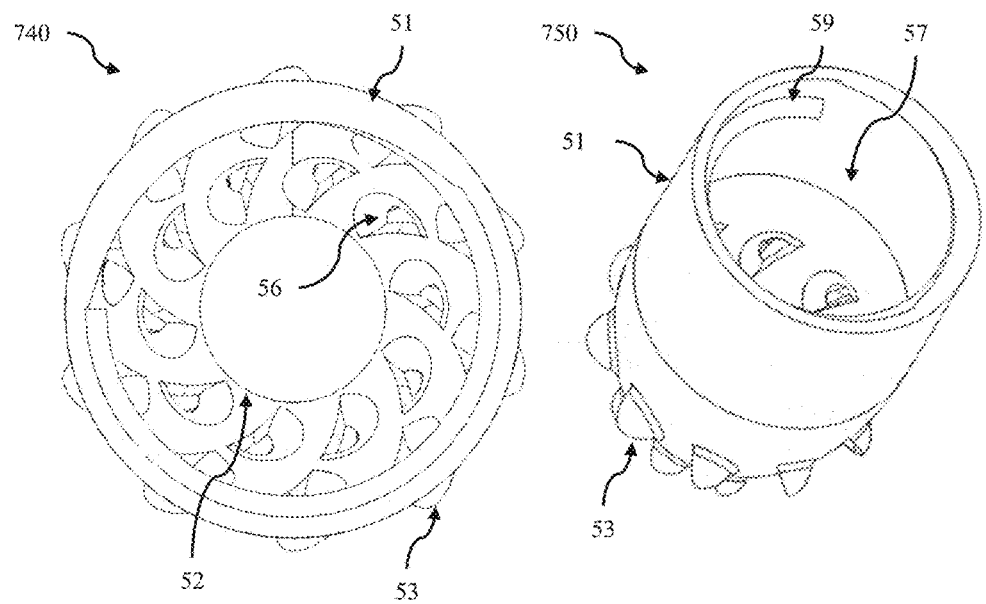
FIG. 7E is a top view of the decorticator apparatus of FIG. 7A.
FIG. 7F is another side isometric view of the decorticator apparatus of FIG. 7A.

FIG. 7A is an isometric end view of a decorticator apparatus 50 according to an embodiment. FIG. 7B is an isometric view 710 of the decorticator apparatus 50 of FIG. 7A and a shaft 60 to which the decorticator apparatus 50 can be fitted. FIG. 7C is an end view 720, FIG. 7D is a side isometric view 730, FIG. 7E is a top view 740 and FIG. 7F is another side isometric view 750 of the decorticator apparatus of FIG. 7A. In this embodiment the decorticator apparatus comprises a substantially circular hollow body 51 having a central axis and tapering at a distal end. The decorticator apparatus also comprises a plurality of directional blade projections 53 located at about the periphery at the distal end. Each blade projection comprises a cup 55 ending in a cutting edge 54 such that rotation about the central axis in a first direction 722 directs the cutting edge into surrounding tissue to cut the surrounding tissue, and rotation about the central axis in an opposite direction 724 directs the cup into the surrounding tissue, and thus does not cut the surrounding tissue. In this embodiment, in profile, each cup 54 extends over an arc of greater than 90°. Additionally in this embodiment the tip comprises a central aperture 52 and each directional blade projection 53 comprises an aperture 56 extending into a collection cavity 57 in the substantially circular hollow body 51. In use at least a portion of the material cut from surrounding tissue is collected within the collection cavity 57, and can then be used to pack the one graft scaffold arrangements. As shown in FIG. 7B the proximal end of the body 51 comprises a thread or channel 59 to allow attachment to standard dilator tube 60 which comprises a central aperture 61 and matching threads 62 at a distal end, for example which is used to tap holes for the pedicle screws or for screwing in (ie insertion) of the pedicle screws. As mentioned above, the directionality of the blades allows the surgeon to control when cutting is performed in order to minimise any damage to surrounding tissue whilst delivering the decorticator to the target decortication site. Thus to deliver the decorticator to the decortication site, the decorticator is attached to the dilator tube, or another delivery tool, which is then inserted into the key hole. When inserting the decorticator through the key hole insertion, and when navigating the decorticator to the target site, the decorticator can be pushed and gently rotated in the non-cutting direction as it is inserted (eg anticlockwise) to prevent damage to surrounding tissue. Once at the target site it can be rotated in the cutting direction (eg clockwise) to decorticate the target site. In one embodiment the decorticator can be provided with a sheath to further protect surrounding tissue during insertion. When near the target site the sheath is retracted to expose the decorticator, which can then be safely navigated to the target site by rotation in the non-cutting direction. Once again, when at the target site the decortication is performed by rotation in the cutting direction. Further once decortication is completed, the decorticator, and any captured bone material, can be extracted by withdrawing the decorticator whilst rotating in the non-cutting direction.

Figure 8A:
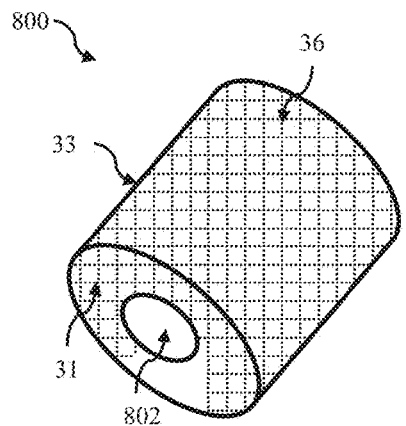
FIG. 8A is an isometric view of a bone graft scaffold apparatus according to an embodiment.
Figure 8B:
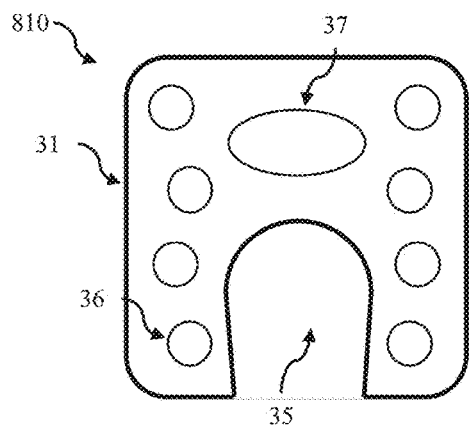
FIG. 8B is an end view of a bone graft scaffold apparatus according to an embodiment.

Other embodiments and variations of the bone graft scaffold apparatus can also be provided. FIGS. 8A to 9E show various alternative embodiments and variations. FIG. 8A is an isometric view 800 of a bone graft scaffold apparatus according to an embodiment. In this embodiment the scaffold apparatus is a tubular structure with openings in the first 31 and second side 32 walls and a central shaft 802 to receive a rod 28 or shaft of a pedicle screw 22. In the case of a rod 28, the tubular structure can be placed on the rod, and the rod and tubular structure placed or inserted between pedicle screws. In this embodiment the tubular structure is a mesh structure. In other embodiments the profile or shape of the clips can be varied. FIG. 8B is an end view 810 of a bone graft scaffold apparatus according to an embodiment. In this embodiment the side profile is substantially square, but other shapes or profiles including elliptical, regular polygons such a rectangular or trapezoidal binder type clip, or irregular polygons can be used.

In one embodiment the bone graft scaffold arrangement has a lattice like or honeycomb structure with bone growth promoting materials located either within the interior of the lattice or coated on the lattice structure. In one embodiment the rod and scaffold arrangement are constructed as a unitary piece such as a cylindrical outer wall structure comprising apertures around a solid rod core, with an annular cavity formed between the outer wall and solid rod core. For example as shown in FIG. 8A in which the central shaft is replaced with a solid rod that extends past the ends of the outer wall (ie for engagement with pedicle screws). The clips may be attached using an applicator tool which releasably grips the clip and can be used to attach the clip to the rod. One fitted the clips can be rotated to a desired orientation, or moved axially along the rod to a desired position. In one embodiment the applicator tool contains projections designed to mate with one or more apertures in the clip to allow the clip to be securely held and moved. In some cases it may be desirable or become necessary to later remove the rod. This may occur after or even during formation of the bone bridge. This process may be assisted by rotating the clips after attachment so that open portion of each clip is directed upward away from the spine to facilitate access to the rod for easier removal.

Figure 8C:
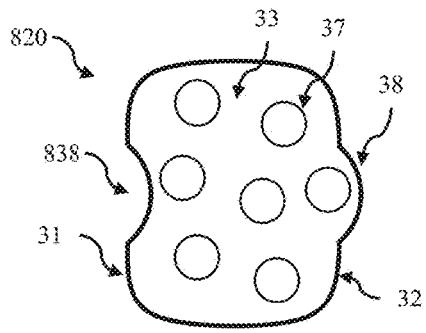
FIG. 8C is a top view of a bone graft scaffold apparatus according to an embodiment.

Additionally or alternatively, a range of attachment projections can be used. FIG. 8C is a top view 820 of a bone graft scaffold apparatus according to an embodiment. In this embodiment, rather than use the shelf and flange illustrated in FIG. 5D, the projection is a curved projection 38 and the opposing side of the housing (when viewed from the top) is cut away 838 to match the curve, so that adjacent clips can be nested. Additionally the curvature can match the curvature of the crown 24. Additionally individual projections in the first side and matching apertures in the second side could be used.

Figure 8D:
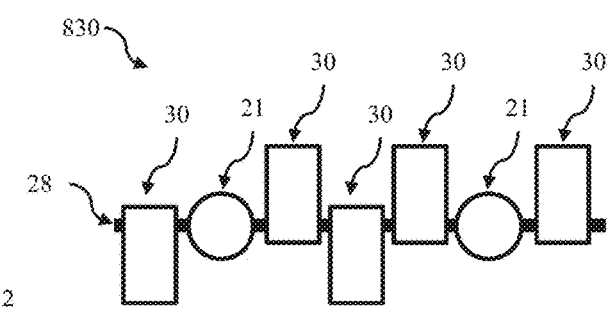
FIG. 8D is a top view of a plurality of bone graft scaffold apparatus attached to a rod according to an embodiment.

Additionally or alternatively, the clips need not be centrally located on the rod. FIG. 8D is a top view 830 of a plurality of bone graft scaffold apparatus 30 attached to a rod 28 according to an embodiment. In this embodiment each clip is clipped onto the rod at a periphery of the clip ie the opening 35 does not extend into the middle portion of the clip. Clips can thus be staggered either side of the rod as shown in FIG. 8D. Further embodiments of clips can be provided which clip around or over the crown of the pedicle screw.

In the embodiment shown in FIG. 4A to 4C the apertures are formed between spokes and ribs. However in other embodiments the washer 40 could be constructed of a mesh or have an irregular network of apertures. In another embodiment the washer could be constructed of a solid material so that insertion of the screws forces the crown into the washer cavity and thus force bone growth material out of and over the sides of the washer cavity into the surrounding tissue. Similarly in one embodiment the washer is formed from a compressible material infused with bone growth promoting materials so that insertion of the screw forces the crown into the washer, and thus forces some of the bone growth promoting materials to leak out into the surrounding tissue.

Figure 9A:
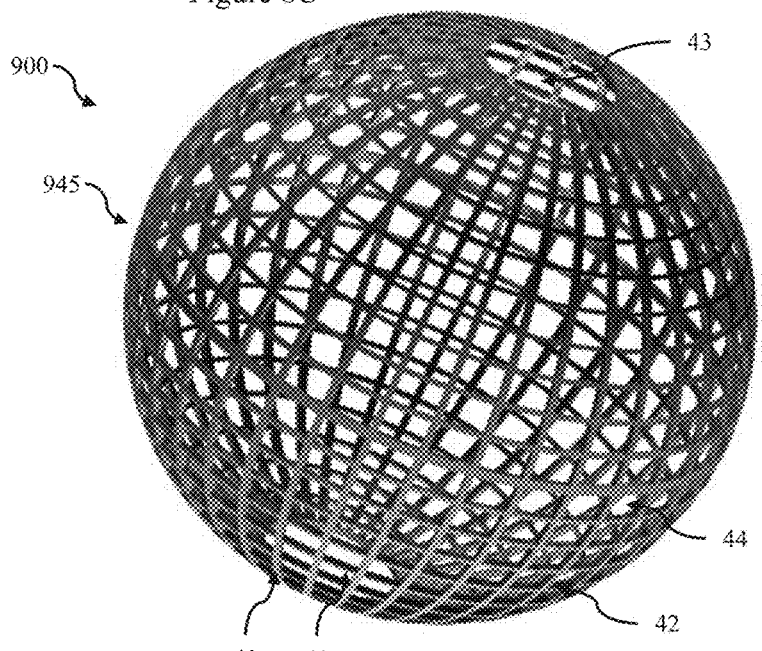
FIG. 9A is an isometric view of an ellipsoid cage embodiment of a bone graft scaffold apparatus according to an embodiment.
Figure 9B:
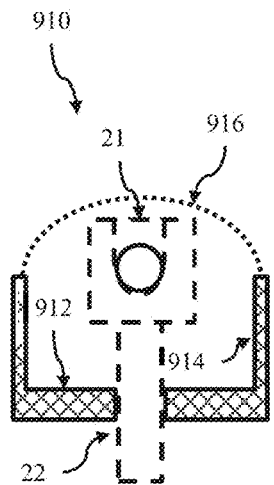
FIG. 9B is a side view of a bone graft scaffold apparatus according to an embodiment.

In another embodiment, the washer 40 can be provided with a cap. This cap may be located over the top surface or top edge 45 of the washer and may be flat or curved. In another embodiment, the cap may extend from the top edge 45 of the washer and extend over and cover the crown 24. The cap may be constructed of the same material of the washer, and may comprise apertures to allow bone growth promoting material to move out into the surrounding tissue through the apertures or to allow bone to grow through the apertures. The apertures may be holes or slits in a rigid housing, or the apertures may be apertures in a mesh, or the material may be porous to allow material to leak out. In one embodiment the cap may be solid and placed over the washer to prevent escape of bone growth promoting material during delivery and be designed so that upon insertion of the screw, the cap can be manually separated from the washer (ie by the surgeon), or separates from the washer to allow bone growth promoting material to escape the washer, for example due to increased internal pressure as the base of the crown moves towards the washer, or due to a mechanism linked to the rotation of the screw or due to deformation of the washer as the screw is inserted into the pedicle. In one embodiment the cap is formed into a spherical or ellipsoidal arrangement, either as a single body or by using two washers end to end. FIG. 9A is an isometric view 900 of an ellipsoid cage embodiment of a bone graft scaffold apparatus according to an embodiment. The washer comprises two central apertures 43 which can be used to fill the washer 40 prior to insertion of screw shaft 22. FIG. 9B is a side view of a bone graft scaffold apparatus according to an embodiment in which the washer is a substantially flat plate 912 with central aperture 43 and an upturned portion 914 extending away from the central aperture to define the cavity. A cap 916 can be placed over the washer 40. In another embodiment, the upturned portion may be provided over a portion of an arc around the shaft, for example 180° or 270°. This would allow the washer version to be clipped onto the shaft of the pedicle screw rather than inserted over the end.

Figure 9C:
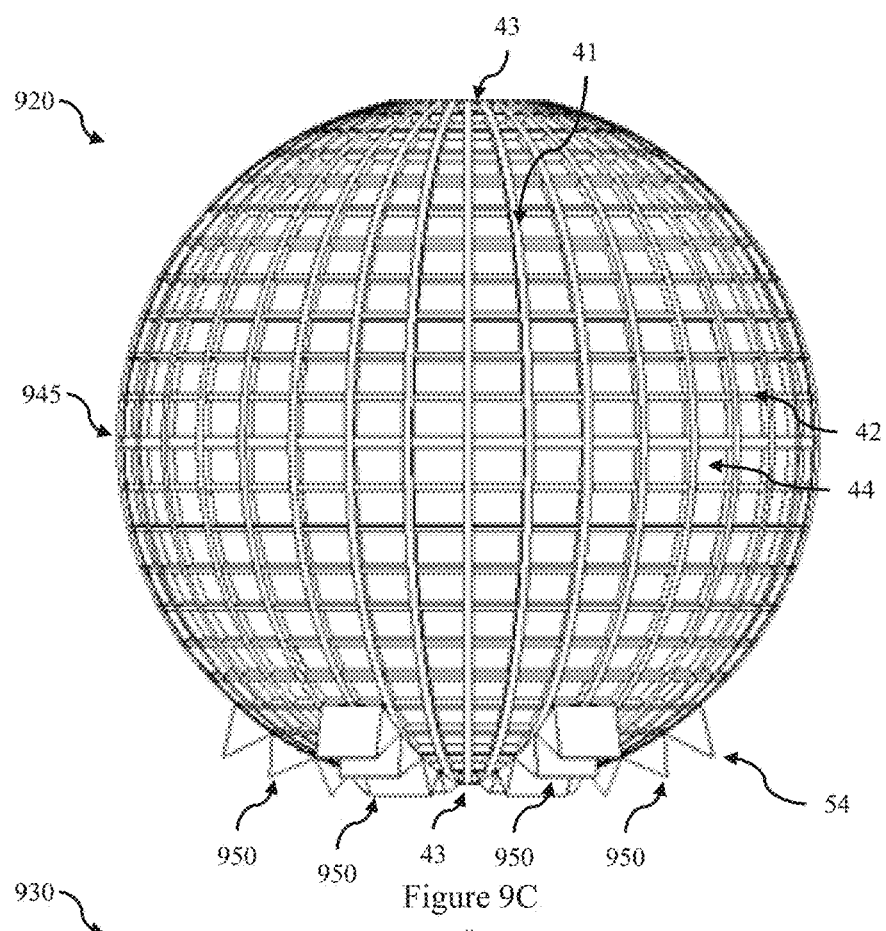
FIG. 9C is a side view of the ellipsoid cage embodiment of FIG. 9A further comprising decorticator blades according to an embodiment.
Figure 9D:
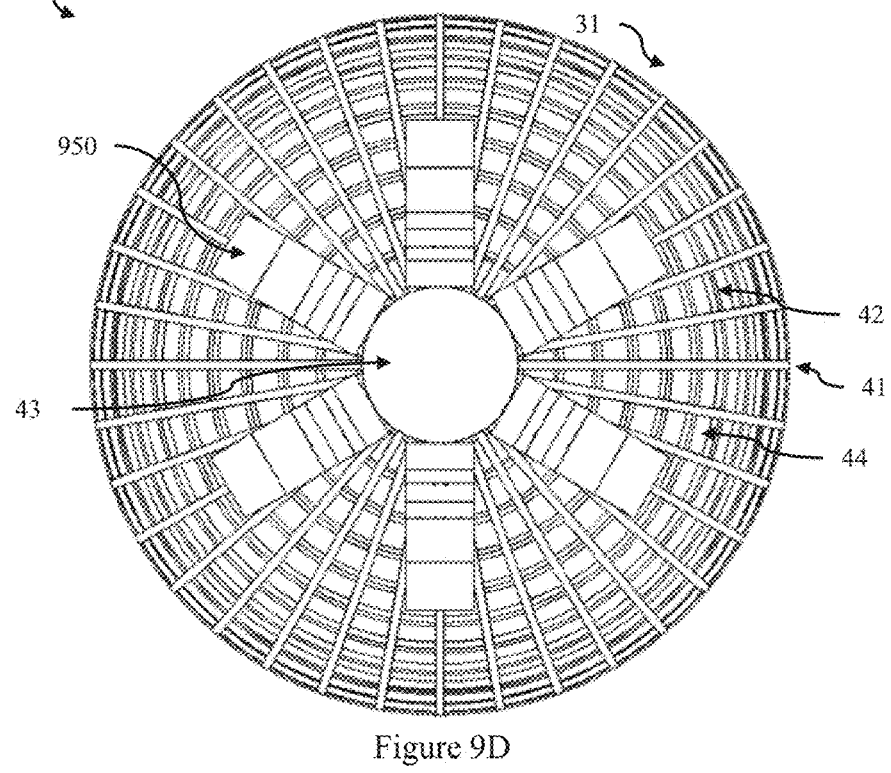
FIG. 9D is an end view of the ellipsoid cage embodiment of FIG. 9A further comprising decorticator blades according to an embodiment.

In another embodiment, the washer 40 could further comprise a plurality of cutting projections projecting from the base of the upturned portion adjacent the shaft. This would allow decortication to be performed as the screw is inserted. FIG. 9C is a side view 920 of the ellipsoid cage embodiment of FIG. 9A further comprising decorticator blades 950 according to an embodiment. FIG. 9D is an end view of the ellipsoid cage embodiment of FIG. 9A and FIG. 9E is a perspective view of a pedicle screw arrangement fitted with the ellipsoid cage embodiment of a bone graft scaffold apparatus of FIGS. 9C and 9D and clip embodiments of a bone graft scaffold apparatus fitted to the rod according to an embodiment. In this form the decorticator blades comprises 6 stepped blades fitted to the base of the washer.

Further the bone graft scaffold arrangements can be manufactured from a range of materials. The bone graft scaffold arrangements may be wholly or partially composed of a biocompatible material such as polyether ether ketone (PEEK) which has excellent biocompatibility, is radio translucent (allowing the growth of the fusion to be imaged), can be readily manufactured and 3D printed. Other biocompatible materials include polymers, carbon fibre, and combinations including carbon fibre infused PEEK, or PEEK infused with radio opaque marker beads (eg tantalum marker beads). Radio opaque biocompatible metals and metal alloys such as titanium, tantalum, Trabecular Metal™ material (Zimmer, Inc., Warsaw, Ind., United States of America) may also be used. In other embodiments the scaffold arrangements could be constructed from bioresorbable material such as a polylactic acid-based material (PLA), a polylactide, polyglycolic acid (PGA) or other bioresorbable materials that slowly degrade and are resorbed over, for example, a period of 12 to 24 months.

In one embodiment, the housing is manufactured from a porous or absorbent material such that prior to use the bone graft scaffold is soaked in a liquid bone growth promoting agent such as liquid Bone Morphogenic Protein (BMP), to absorb the bone growth promoting agent so that in use the bone growth promoting reagent will leach out of the housing. In one embodiment the bone graft scaffold arrangement is a compressible and/or porous material into which bone growth promoting materials are infused prior to delivery, and then leach out either during insertion of the scaffold apparatus, for example as it is compressed by the surrounding tissue, and/or over time after insertion of the rod. In one embodiment the bone growth material may leach out at a desired rate to the surrounding tissue to promote formation of the bony union around, on or through the scaffold apparatus. In one embodiment the housing is a sheet like material with a plurality of holes (apertures) such as illustrated in FIGS. 5A to 5E. In another embodiment, the housing is a mesh and the plurality of apertures are interstitial spaces in the mesh. The mesh may be a titanium mesh, or constructed of another biocompatible (eg PEEK) or bioresorbable material.

The scaffold arrangements are provided or filled with suitable cells and materials to achieve, following surgery, in situ generation of bone bridges between the vertebrae. The bone growth promoting materials may also include biologically active bone growth promoting agents that stimulate stem cells or other cells to develop or differentiate into osteoblasts such as those in the Bone Morphogenic Protein family (BMPs). For example the cavities could be packed with Mastergraft® granules (BioHorizons) mixed with autologous blood was then packed into the cavities of the device. In one embodiment the bone growth promoting material includes pieces or particles of a biocompatible porous or sponge like material that has been soaked in a liquid solution containing BMPs. Suitable cells include those that are capable of differentiating into bone-like cells such as osteoblasts, and in one embodiment the cells include bone fragments. Examples of such cells are stem cells including mesenchymal stem cells and cells contained in bone fragments, such as those obtained in the decortication process. The cells may be autologous. The slot 37 or central aperture 43 can act as a port for injection or placement of bone graft promoting materials in the cavities of the bone graft scaffold apparatus. The bone graft scaffold apparatus can be preloaded with bone graft promoting materials prior to placement, or they may be first inserted into the body and then filled, for example by injection via the ports 37 or open cavity in the washer. In one embodiment, the housing is manufactured from a porous or absorbent material such that prior to use the bone graft scaffold is soaked in a bone growth promoting agent to absorb the bone growth promoting agent so that in use the bone growth promoting reagent will leach out of the housing, or be forced out during insertion due to pressure from the surrounding tissue.

The scaffold arrangements may be provided with a therapeutically effective amount of cells in combination with an agent such as BMP and/or a pharmaceutically-acceptable carrier within cavities of the scaffold arrangements. Optionally, the cells and/or BMP may be retained in the cavities with, for example, a substance such as fibrin glue (eg Tisseel; Baxter International Inc, Deerfield, Ill., United States of America), Gelfoam® (Pharmacia & Upjohn Company, New York, N.Y., United States of America) or other biocompatible scaffold or matrix material, or a thin film of biodegradable material. Otherwise, the pharmaceutically-acceptable carrier can be adapted to retain the cells and/or BMP in the cavity. In this manner, the scaffold arrangements act as a cell delivery vehicle. The term "therapeutically effective amount" as used herein is to be understood as referring to an amount of the cells (ie a cell number) that is viably sufficient for the in situ generation of bone growths between the vertebrae along the path of the rod. Such an amount may vary considerably depending upon a range of factors such as the mode of administration, and the age and/or body weight of the subject and presence of other factors such as BMPs and similar agents.

Additionally the scaffold structures and structural components such as rods and screws may also be coated with a composition comprising one or more biologically active agents for stimulating differentiation of cells into a bone cells (eg osteoblasts). In one embodiment bone growth promoting materials are layered on the rod and covered by a suitable covering material. The covering material may be biodegradable so as to dissolve within the body at a known rate to deliver the bone growth promoting material direct to the required site adjacent the rod, or alternatively the desired covering may be permeable to allow the bone growth promoting materials to leach out. Further the surface of the scaffold apparatus may be surface treated or textured to promote bone growth. Embodiments of the bone graft scaffold arrangements thus allow delivery of bone growth promoting materials in directed and targeted locations to promote formation of a bony union along a desired path.

In the embodiments described above the rod 28 is a solid allowing use with existing components. However in one embodiment a hollow rod is used as a container or delivery mechanism for the bone graft material, and may be in addition to other scaffold arrangements such as clips or washers, or instead of other scaffold arrangements such as clips or washers. A hollow rod can also be used as an injector to allow injection of bone graft material as the rod is inserted between pedicle screws and thus along the desired bone growth path. Thus in one embodiment bone graft promoting material is injected into the rear end of the rod as the rod in inserted through the tissue between pedicle screws so that bone growth promoting material extrudes or flows out from the bore in the leading or front end (or tip) of the rod. This assist in laying a continuous path of bone growth promoting material alongside the rod (eg the interstitial space) and between the pedicle screws to assist in creation of a bony bridge between screws in a minimally invasive way. Additionally or alternatively the rod can also be coated with bone growth promoting material.

As the rod is a structural component, inserting a bore will weaken the strength of the rod depending upon the relative diameter of the bore to the rod diameter and specific material properties of the rod. Thus selection of the size of the rod and bore will need to take into account the required strength of the rod, and an appropriate rod and bore size can be selected to match this requirement. In some cases a larger diameter hollow rod may be selected in place of a smaller diameter solid rod that could be used to ensure required structural strength is achieved whilst also allowing delivery of bone growth promoting material along the path. Determination of an appropriate bore diameter can be performed by direct material testing experiments and/or by an analytical or numerical Finite Element Analysis (FEA) method as is discussed below.

In one embodiment the structural strength of a 5.5 mm outer diameter titanium rod constructed of Ti-6AL-4V ELI was assessed using a finite element analysis (FEA) simulation approach of compression and bending tests according to ASTM F1717-14. The material was assumed to be uniform, isotropic, and linearly elastic with smooth surfaces. Material properties used for the simulation were based on published values of a density of 4.43 g/cc, a modulus of elasticity of 113.8 GPa, an ultimate tensile strength of 860 MPa, a yield tensile strength of 790 MPa, a compressive yield strength of 860 MPa and a Poisson Ration of 0.342. The basic test setup simulated is comprised of two rods fixed to four pedicle screws mounted to two polyethylene blocks. The polyethylene blocks are pin jointed to an axial compression rig with the axis of rotation around 50 mm from the vertically mounted rod. Axial compression of the test rig generates a bending moment and axial compression force in the spinal implant rod. The force at which yield occurs is used to evaluate the strength of the spinal construct. A decrease in yield load indicates a decrease in strength.

Since the geometry of the rods and the loading conditions are simple, compressive bending was modelled analytically rather than numerically. The analytical solution was derived from fundamental bending equations and solutions to peak stresses for round bars according to W. D. Pilkey and D. F. Pilkey, "Holes," in Peterson's Stress Concentration Factors, John Wiley and Sons, 2008, pp. 176-400. In this analysis a round hollow rod of outer diameter D, and inner diameter d, is placed under a compressive bending load comprising a bending moment, M and compressive force, F. The maximum magnitude of bending stress ($\sigma_{max\_bend}$) occurs at the upper and lower extremities of the bar, and is calculated using the formula: $\sigma_{max\_bend}$=MD/2I where I is the moment of inertia of the cross sectional area of the hollow bar. The compression stress ($\sigma_{max}$) is uniform throughout the rod, and is calculated using the formula $\sigma_{comp}$=F/A, where A is the cross sectional area of the bar. The maximum compressive stress magnitude can be determined through superposition of the maximum bending stress in compression and compressive stress $\sigma_{max}=\sigma_{max\_bend}+\sigma_{max}$. Analysis of compressive bending was performed for solid rods and hollow rods with an inner (bore) diameter from 0 to 3.5 mm for a rod with an outer diameter of 5.5 mm (ie a bore with a diameter 63% of outer diameter).

Analysis of the compression stresses from the lock screw was performed using FEA numerical simulation using the ANSYS Workbench Mechanical Simulation package. The rod was modelled as a hollow cylinder with a variable bore, and the lock screw was modelled as a solid cylinder with the flat surface tangent to the rod. Stresses due to lock screw compression on a hollow rod were simulated using ANSYS Mechanical Simulation 2015. Lock screw compression was 10 kN approximated from 10 Nm of torque on a Nuvasive Precept lock screw. To counteract artificial peak stresses at contact points, peak stress was taken as the 95th percentile of stresses in the rod occurring greater than 0.5 mm from the contact point.

Calculations showed a single solid 5.5 mm diameter rod under compressive bending is expected to yield at around 255 N loading force, which is consistent with the benchmark value of 496 N provided in the ASTM F1717-14 standard for two 5.5 mm rods of stainless steel. Compressive bending of the hollow rod showed an exponential decrease in the yield load with increasing bore diameter. This trend shows little change to around 1.5 mm bore diameter, then a decreasing yield load as the bore size increased −1.5% decrease at 2 mm, 3% at 2.225 mm, 4% at 2.5 mm, 6% at 2.75 mm and 8.5% at 3 mm, 12.5 % at 3.25 mm and 15.5% at 3.5 mm. Finite element analysis of compressive loading of a hollow rod shows little change in peak stresses from a solid rod to a hollow rod of up to around 2 mm bore diameter, after which there is a rapid increase in peak stress with the yield limit being reached at around 2.45 mm. Overall the results suggest that for a 5.5 mm rod, a bore of up to 2 mm diameter may exhibit similar structural performance to a solid rod.

Generalising this suggests a bore diameter of up to 40% of the outer rod diameter may be used without significant loss of structural performance.

In a further embodiment, transverse dispersion holes are provided around the front end or tip of the rod. In use this front end or tip extends past the pedicle screws, and thus insertion of transverse dispersion holes will not significantly weaken the structural strength of the rod. Thus as the hollow rod is inserted between pedicle screws, bone graft promoting material can be inserted in the rear of the rod and the transverse dispersion holes will further assist in introducing or dispersing bone graft promoting material around the path of the rod to further facilitate growth of a continuous bony bridge. Additionally the rod can also be coated with bone growth promoting material and/or bone graft scaffold arrangements can be attached to the rod.

FIG. 10A is a side profile view 1000 of an end of a hollow rod according to an embodiment and FIG. 10B is an end view 1010. The rod 28 has an outer diameter 1002 comprises a bore 1004 with a bore diameter 1006 (which is less than the outer diameter 1002). Additionally a series of transverse channels 1008 or spout or dispersion holes are provided near the tip to allow bone graft material to disperse around the tip. These may be straight or curved channels. FIG. 10C is a three-quarter section view of an end of a hollow rod showing a spout hole arrangement for bone graft material dispersion according to an embodiment. In one embodiment the bore 1004 extends from the rear end of the rod and ends in spouts and is blocked at the tip end. This may assist in preventing prevent clogging of the bore as it is inserted through tissue.

The bone graft scaffold arrangements can be supplied individually as modular components or provided as a kit or orthopaedic device comprising:
 at least one rod;
 at least two pedicle screws;
 a plurality of bone graft scaffold apparatus as described herein.

The embodiments described herein also provide a method for performing surgery. This is for example illustrated in FIGS. 6A to 6D. This method comprises:
 filling one or more bone graft scaffold apparatus with bone growth promoting materials;
 inserting a first pedicle screw into a pedicle of a first vertebra;
 inserting a second pedicle screw into a pedicle of a second vertebra;
 inserting a rod between the first pedicle screw and the second pedicle screw; and
 attaching the one or more graft scaffold apparatus to the rod, the first or the second pedicle screw.

The scaffold arrangements are suitable for use in MIS posterolateral spinal fusion procedures. However as would be understood by the person skilled in the art, they may also be used in other surgical procedures including open surgery posterolateral spinal fusion, as well as in minimally invasive and open procedures where it is desirable to promote bone growth around structural elements such as in interbody spinal fusion. These implants are also suitable in situations where there is a gap in the bone to promote bony fusion over the gap. This can occur in the case of surgery to treat bone tumour metastasis. Thus in one embodiment a rod could be placed across the gap to span the cavity, and bone graft scaffold apparatus can be attached to the rod. Also in some cases it is desirable to direct growth along a certain path, for example away from neural elements. In such cases rods and screws can be inserted to which bone graft scaffold apparatus can be attached in order to create a desired growth path.

Embodiments of the bone graft scaffold apparatus comprise a housing which comprises a cavity for receiving bone growth promoting materials and a plurality of apertures. In use these allow bone growth promoting material to move out into the surrounding tissue through the plurality of apertures and/or to allow bone (and blood vessels) to grow through the plurality of apertures to form the bone bridge between vertebrae. Embodiments of the bone graft scaffold arrangements can be inserted through the key-hole incision, clipped onto the in situ rods, and pushed through the region between key-hole incisions, which would otherwise be inaccessible. Once fitted on the rod the clips can be rotated and/or moved axially along the rod. The bone graft scaffold apparatus can be constructed from a biocompatible radio translucent polymer such as PEEK. The bone graft scaffold arrangements described herein are used as scaffold structures to assist in the formation of the bone bridge, and as such do not need to be structural components like the rods and screws. Thus the housing of the bone graft scaffold arrangements may be supported by the shaft. In some embodiments a bore may be provided in a rod to allow injection of bone growth promoting material as the rod is inserted between pedicle screws (ie along the desired growth path). The apparatus can be attached to structural components such as rods and screws and used to form a continuous scaffold between vertebras to assist in forming a bone bridge along a desired path. Similarly embodiments can be used to control or direct growth along a desired path, for example away from neural or other tissue.

The decortification devices described have the advantage that they are compact and have a cross sectional area no greater than the pedicle screw towers currently used in the MIS procedure (~20 mm diameter). Further they are able to be inserted to the decortication site and to function with minimal damage to surrounding muscle and tissue, and are able to be operated by the surgeon from outside the patient without direct vision of the site. Further they are able to be integrated into the current spinal fusion fixation systems in use (e.g. Medtronic Horizon, Nuvasive Precept), are robust enough to not break or fail during use, and are able to decorticate varying bone geometries considering variances between individuals and variances between vertebrae levels.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the disclosure is not restricted in its use to the particular application or applications described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope as set forth and defined by the following claims.

What is claimed is:

1. A bone graft scaffold clip for use in performing minimally invasive posterolateral spinal fusion where a first pedicle screw is inserted into the pedicle of a first vertebra and a second pedicle screw is inserted into the pedicle of a second first vertebra, and a rod is inserted between the first and second pedicle screw and the tissue surrounding the rod and between the first and second pedicle screws is not exposed, the clip comprising a housing configured to clip onto the shaft of the rod such, that in use, the shaft supports the housing, and the housing further comprises:
- a first side wall,
- an opposing second side wall, and
- an outer wall spanning the first side wall and opposing second side wall and comprising an opening extending inward from the outer wall to receive the shaft such that in use the received shaft extends through the first side wall and the opposing second side wall,
- a cavity defined by the first side wall, second side wall and outer wall for receiving bone growth promoting materials via the opening; and
- a plurality of apertures in at least the outer wall, which in use allow bone growth promoting material to move out into the surrounding tissue through the plurality of apertures and/or to allow bone to grow through the plurality of apertures.

2. The bone graft scaffold clip as claimed in claim 1 wherein the clip further comprises an inner surface wherein the inner surface is largely open and defined by a plurality of ribs extending between the first and second side walls to allow bone graft material in the cavity in the housing to contact the rod and the radius of the inner wall surface is selected to approximately match a diameter of the rod.

3. The bone graft scaffold clip as claimed in claim 1, wherein the housing is a C shaped clip structure.

4. The bone graft scaffold clip as claimed in claim 1, wherein the housing further comprises an attachment projection from the first side wall, and a corresponding receiving structure on the second side wall, such that in use, the attachment projection from a first bone graft scaffold clip engages with the receiving structure in a second adjacent bone graft scaffold clip to secure and align the first and second bone graft scaffold clips.

5. The bone graft scaffold clip as claimed in claim 4, wherein the attachment projection comprises a shelf and a flange, and the receiving structure comprises a slot for receiving the flange.

6. The bone graft scaffold clip as claimed in claim 1, wherein the housing is manufactured from a porous or absorbent material such that prior to use the bone graft scaffold clip is soaked in a bone growth promoting agent to absorb the bone growth promoting agent so that in use the bone growth promoting reagent will leach out of the housing.

7. The bone graft scaffold clip as claimed in claim 1, wherein the housing is a mesh and the plurality of apertures are interstitial spaces in the mesh.

8. The bone graft scaffold clip as claimed in claim 1, wherein the bone graft scaffold apparatus is coated with a bone growth promoting agent.

9. The bone graft scaffold clip as claimed in claim 1, wherein the bone graft scaffold apparatus is constructed from a biocompatible radio translucent polymer.

10. An orthopaedic system for performing minimally invasive posterolateral spinal fusion comprising:
- at least one rod comprising a shaft;
- at least two pedicle screws, each comprising a threaded shaft and adapted to receive and lock the rod in place such that in use the shaft of the rod spans the at least two pedicle screws;
- a plurality of bone graft scaffold clips, each clip comprising a housing configured to clip onto the shaft of the rod such that the shaft supports the housing, and the housing further comprises:
  - a first side wall,
  - an opposing second side wall, and
  - an outer wall spanning the first side wall and opposing second side wall and comprising an opening extending inward from the outer wall to receive the shaft such that in use the received shaft extends through the first side wall and the opposing second side wall,
  - a cavity defined by the first side wall, second side wall and outer wall for receiving bone growth promoting materials; and
  - a plurality of apertures in at least the outer wall, which in use allow bone growth promoting material to move out into the surrounding tissue through the plurality of apertures and/or to allow bone to grow through the plurality of apertures.

11. A method for performing minimally invasive posterolateral spinal fusion surgery comprising:
- filling one or more bone graft scaffold clips with bone growth promoting materials, wherein each bone graft clip comprise a housing configured to clip onto the shaft of a rod such that the shaft supports the housing, and the housing further comprises:
  - a first side wall,
  - an opposing second side wall, and
  - an outer wall spanning the first side wall and opposing second side wall and comprising an opening extending inward from the outer wall to receive the shaft such that in use the received shaft extends through the first side wall and the opposing second side wall,
  - a cavity defined by the first side wall, second side wall and outer wall for receiving bone growth promoting materials via the opening; and
  - a plurality of apertures in at least the outer wall, which in use allow bone growth promoting material to move out into the surrounding tissue through the plurality of apertures and/or to allow bone to grow through the plurality of apertures;
- making a first incision to access a pedicle of a first vertebra;
- making a second incision to access a pedicle of a second vertebra;
- inserting a first pedicle screw into the pedicle of the first vertebra;
- inserting a second pedicle screw into the pedicle of the second vertebra;
- inserting a rod between the first pedicle screw and the second pedicle screw, wherein the tissue surrounding the rod and between the first and second pedicle screws is not exposed; and
- clipping a first bone graft scaffold clip to a shaft of the rod adjacent the first pedicle screw and between the first and second pedicle screws via the first incision such that the shaft of the rod supports the clip, and
- clipping one or more further bone graft scaffold clips to the shaft of the rod adjacent the first pedicle screw and between the first and second pedicle screws via the first incision such that the shaft of the rod supports the clip, wherein prior to clipping each of the one or more further graft scaffold clips to the shaft, the scaffold clips clipped onto the shaft are pushed along the rod toward the second pedicle screw.

12. The orthopaedic system as claimed in claim 10, wherein the clip further comprises an inner surface wherein the inner surface is largely open and defined by a plurality of ribs extending between the first and second side walls to allow bone graft material in the cavity in the housing to contact the rod and the radius of the inner wall surface is selected to approximately match a diameter of the rod.

13. The orthopaedic system as claimed in claim 10, wherein the housing further comprise an attachment projection from the first side wall, and a corresponding receiving structure on the second side wall, such that in use, the attachment projection from a first bone graft scaffold clip engages with the receiving structure in a second adjacent bone graft scaffold clip to secure and align the first and second bone graft scaffold clips.

14. The orthopaedic system as claimed in claim 10, wherein the system further comprises a conical washer and comprising a central aperture configured to receive the threaded shaft of the pedicle screw and at least one upturned portion extending away from the central aperture and having a plurality of apertures and having a rotationally symmetric upwardly curved profile to define a cavity for receiving bone growth promoting materials.

15. The orthopaedic system as claimed in claim 14 further comprising a cap.

16. The orthopaedic system as claimed in claim 14 further comprising a plurality of cutting projections projecting from a base from the upturned portion adjacent the shaft.

17. The orthopaedic system as claimed in claim 10 wherein the housing of the bone graft scaffold clips is manufactured from a porous or absorbent material such that prior to use the bone graft scaffold is soaked in a bone growth promoting agent to absorb the bone growth promoting agent so that in use the bone growth promoting reagent will leach out of the housing.

18. The orthopaedic system as claimed claim 10, wherein the housing is a mesh and the plurality of apertures are interstitial spaces in the mesh.

19. The orthopaedic system as claimed in claim 10, wherein the housing is coated with a bone growth promoting agent.

20. The orthopaedic system as claimed in claim 10, wherein the housing is constructed from a biocompatible radio translucent polymer.

21. The orthopaedic system as claimed in claim 10, wherein the rod and pedicle screws are structural components and the plurality of bone graft scaffold clips are non structural components.

22. The method as claimed in claim 11, wherein each bone graft scaffold clip further comprises an attachment projection from the first side wall, and a corresponding receiving structure on the second side wall, and when clipping one or more further bone graft scaffold clips to the shaft of the rod the attachment projection from the further bone graft scaffold clip being clipped engages with the receiving structure in the bone graft scaffold clip of the previous clip to secure and align the bone graft scaffold clips together.

23. The method as claimed in claim 11, wherein prior to inserting the first pedicle screw in the pedicle of the first vertebra a shaft of the first pedicle screw is inserted into a conical washer, and the conical washer comprises a central aperture configured to receive the shaft of the first pedicle screw and at least one upturned portion extending away from the central aperture and having a plurality of apertures and having a rotationally symmetric upwardly curved profile to define a cavity for receiving bone growth promoting materials, and prior to inserting the second pedicle screw in the pedicle of the second vertebra a shaft of the second pedicle screw is inserted into a conical washer, and the conical washer comprises a central aperture configured to receive the shaft of the second pedicle screw and at least one upturned portion extending away from the central aperture and having a rotationally symmetric upwardly curved profile to define a cavity for receiving bone growth promoting materials, and the method further comprises the step of placing bone growth promoting materials in the cavity of each conical washer.

* * * * *